United States Patent [19]

Hamilton et al.

[11] Patent Number: 4,616,003
[45] Date of Patent: Oct. 7, 1986

[54] N[6]-DIHYDROXYPROPYLADENOSINES

[75] Inventors: Harriet W. Hamilton; William C. Patt, both of Chelsea, Mich.

[73] Assignee: Warner-Lambert Company, Morris Plains, N.J.

[21] Appl. No.: 771,589

[22] Filed: Sep. 5, 1985

Related U.S. Application Data

[63] Continuation-in-part of Ser. No. 665,229, Oct. 26, 1984, abandoned.

[51] Int. Cl.$^4$ .............................................. A61K 31/70
[52] U.S. Cl. ......................................... 514/46; 536/26
[58] Field of Search ............................ 536/26; 514/46

[56] References Cited

U.S. PATENT DOCUMENTS 4,388,308  6/1983  Hamilton .............................. 536/26

FOREIGN PATENT DOCUMENTS 2077726  12/1981  United Kingdom .................. 536/26

OTHER PUBLICATIONS

J. Radiat. Res., 15,19 (1974), H. Askuto, et al.

Primary Examiner—Ethel G. Love
Attorney, Agent, or Firm—Joan Thierstein

[57] ABSTRACT

N[6]-Dihydroxypropyladenosines and pharmaceutically acceptable acid addition salts having highly desirable central nervous system properties, processes for their manufacture and pharmaceutical compositions and methods for using said compounds and compositions are described.

15 Claims, No Drawings

N⁶-DIHYDROXYPROPYLADENOSINES

This is a continuation-in-part of U.S. application Ser. No. 06/665,229, filed Oct. 26, 1984, now abandoned.

BACKGROUND OF THE INVENTION

2-Hydroxypropyladenosine has been described in the literature as a radioprotective agent by H. Askura, et al, in *J. Radiot. Res.*, 15, 19 (1974).

The present dihydroxypropyladenosines have valuable sedative/hypnotic properties and are useful for treating sleep disorders.

SUMMARY OF THE INVENTION

Accordingly the present invention relates to a compound of the formula:

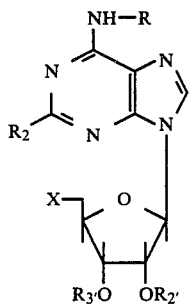

wherein R is

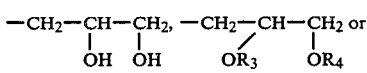

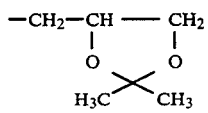

wherein $R_3$ and $R_4$ are the same or different and are lower alkanoyl, benzoyl, or benzoyl substituted by lower alkyl, lower alkoxy, halogen, or trifluoromethyl; $R_2$ is H, $NH_2$, $NHR_6$ where $R_6$ is alkanoyl, benzoyl, or benzoyl substituted by lower alkyl, lower alkoxy, halogen, or trifluoromethyl; or halogen; $R_2'$ and $R_3'$ are each independently H, lower alkanoyl, benzoyl, or benzoyl substituted by lower alkyl, lower alkoxy, halogen, or trifluoromethyl, or when taken together lower alkylidene, such as isopropylidene; X is OH, acetyloxy, H, Cl, $SCH_3$, or $OR_5'$ wherein $R_5'$ is H, lower alkanoyl, benzoyl, benzoyl substituted by lower alkyl, lower alkoxy, halogen, or trifluoromethyl; its diastereomers or mixtures thereof, or a pharmaeutically acceptable acid addition salt thereof.

The present invention also relates to a pharmaceutical composition comprising a therapeutically effective amount of a compound of the above Formula I with a pharmaceutically acceptable carrier, and to a method of treating mammals by administering to such mammals a dosage form of a compound of the Formula I as defined above.

DETAILED DESCRIPTION

In the compounds of the Formula I, the term "lower alkyl" is meant to include a straight or branched alkyl group having from 1 to 6 carbon atoms such as, for example, methyl, ethyl, propyl, isopropyl, butyl, sec-butyl, isobutyl, tert-butyl, amyl, isoamyl, neopentyl, hexyl, and the like.

Halogen includes particularly fluorine, chlorine or bromine.

Lower alkoxy is O-alkyl of from 1 to 6 carbon atoms as defined above for "lower alkyl".

Lower alkanoyl is a straight or branched

group of from 1 to 6 carbon atoms in the alkyl chain as defined above.

The compounds of Formula I are useful both in the free base form and in the form of acid addition salts. Both forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compounds of the invention may contain an asymmetric carbon atoms. The invention includes the individual diastereomers and mixtures thereof. The individual diastereomers may be prepared or isolated by methods known in the art.

Another preferred embodiment is a compound of Formula I wherein R is 2,3-dihydroxypropyl and $R_2$, $R_2'$, $R_3'$, and X are as defined above.

Another preferred embodiment is a compound of Formula I wherein R is 2,3-dihydroxypropyl, $R_2$ is hydrogen, and $R_2'$, $R_3'$, and X are as defined above.

Still another preferred embodiment is a compound of Formula I wherein R is 2,3-dihydroxypropyl, $R_2$, $R_2'$, and $R_3'$ are hydrogen, and X is as defined above.

A particular embodiment includes N⁶(2,3-dihydroxypropyl)-adenosine or a pharmaceutically acceptable salt thereof.

The compounds of Formula I may be conveniently synthesized by reacting a 6-halopurine riboside of Formula II with dihydroxypropyl amine or the acetone adduct thereof of Formula III and IIIa in an inert solvent such as alcohol, or an aprotic solvent such as dimethylformamide between about 25° to about 130° C. for from 1–48 hours. It is useful to add a base such as triethylamine, or calcium carbonate to neutralize the hydrogen halide formed as a byproduct of the reaction, but this can also be accomplished by using an extra equivalent of the dihydroxypropylamine. It is also convenient, although not necessary, to protect the ribofuranose hydroxyl groups as acetate or benzoate esters which can be removed with ammonium hydroxide or sodium methoxide following the synthesis of the N⁶- substituted adenosine. The reaction is illustrated as follows:

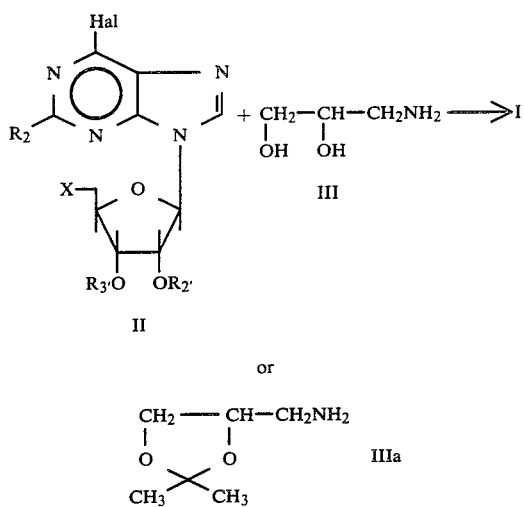

Additionally, a reaction to prepare compounds of the Formula I wherein R is

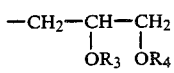

is illustrated as follows:

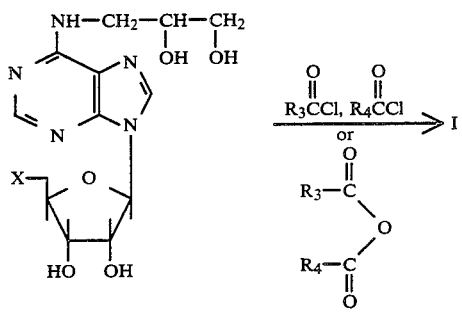

wherein Hal is halogen, preferably chlorine or bromine, and X, $R_2$, $R_2'$, and $R_3$ are as defined for Formula I.

The compounds of Formula I have been found to possess differing affinities for adenosine receptors (designated $A_1$ and $A_2$ receptors for convenience). These compounds are active in animal tests which are predictive of having sedative/hypnotic properties and as such, are useful for the treatment of sleep disorders. These compounds also have analgesic properties and as such, are useful in the treatment of pain.

PHARMACOLOGICAL EVALUATION

Adenosine Receptor Binding—$A_1$ Receptor Affinity (RBA1)

Preparation of Membranes

Whole brain minus cerebellum and brainstem from male Long Evans rats (150–200 g) was homogenized in 30 volumes of ice-cold 0.05M Tris-HCl buffer pH 7.7 using a Brinkman Polytron PT-10, (setting number 6 for 20 seconds) and centrifuged for ten minutes at 20,000×g (Sorvall RC-2), 4° C. The supernatant was discarded, and the pellet was resuspended and centrifuged as before. The pellet was resuspended in 20 ml Tris-HCl buffer containing two International Units/ml of adenosine deaminase (Sigma type III from calf intestinal mucosa), incubated at 37° C. for 30 minutes, then subsequently at 0° C. for ten minutes. The homogenate was again centrifuged, and the final pellet was resuspended in ice-cold 0.05M Tris-HCl buffer pH 7.7 to a concentration of 20 mg/ml original wet tissue weight and used immediately.

Assay Conditions

Tissue homogenate (10 mg/ml) was incubated in 0.05M Tris-HCl buffer pH 7.7 containing 1.0 nM [$^3$H]-$N^6$-cyclohexyladenosine ([$^3$H]-CHA) with or without test agents in triplicate for one hour at 25° C. Incubation volume was 2 ml. Unbound [$^3$H]-CHA was separated by rapid filtration under reduced pressure through Whatman glass fiber (GF/B) filters. The filters were rinsed three times with 5 ml of ice cold 0.05M Tris-HCl buffer pH 7.7. The radio-labeled ligand retained on the filter was measured by liquid scintillation spectrophotometry after shaking the filters for one hour or longer on a mechanical shaker in 10 ml of Beckman Ready-Solv HP scintillation cocktail.

Calculations

Nonspecific binding was defined as the binding which occurred in the presence of 1 mM theophylline. The concentration of test agent which inhibited 50% of the specific binding ($IC_{50}$) was determined by nonlinear computer curve fit. The Scatchard plot was calculated by linear regression of the line obtained by plotting the amount of radioligand bound (pmoles/gram of tissue) versus $$\left[\frac{\text{bound radioligand}}{\text{free radioligand}}\right].$$

Since the amount of radioligand bound was a small fraction of the total amount added, free radioligand was defined as the concentration (nM) of radioligand added to the incubation mixture. The Hill coefficient was calculated by linear regression of the line obtained by plotting the log of the bound radioligand vs the log of the $$\left[\frac{\text{bound radioligand}}{B_{max} - \text{bound radioligand}}\right].$$

The maximal number of binding sites ($B_{max}$) was calculated from the Scatchard plot.

Adenosine Receptor Binding—$A_2$ Receptor Affinity (RBA2)

Tissue Preparation

Brains from 200–500 g mixed sex Sprague-Dawley rats were purchased from Pel-Freez (Rogers, Ark.). Fresh brains from male Long-Evans hooded rats (Blue Spruce Farms, Altamont, N.Y.) gave essentially identical results. Brains were thawed and then kept on ice while the striata were dissected out. Striata were disrupted in 10 vol of ice-cold 50 mM Tris.HCl (pH 7.7 at 25° C., pH 8.26 at 5° C.) (Tris) for 30 seconds in a Polytron PT-10 (Brinkmann) at setting 5. The suspension was centrifuged at 50,000 xg for ten minutes, the supernatant discarded, the pellet resuspended in 10 vol ice-cold Tris as above, recentrifuged, resuspended at 1 g/5 ml, and stored in plastic vials at −70° C. (stable for at least six months). When needed, tissue was thawed at room temperature, disrupted in a Polytron, and kept on ice until used.

Incubation Conditions

All incubations were for 60 minutes at 25° C. in 12×75 mm glass tubes containing 1 ml Tris with 5 mg original tissue weight of rat weight of rat striatal membranes, 4 nM [$^3$H]-N-ethyl adenosine-5'-carboxamide ([$^3$H]NECA), 50 nM N$^6$-cyclopentyladenosine (to eliminate A$_1$ receptor binding), 10 mM MgCl$_2$, 0.1 units/ml of adenosine deaminase and 1% dimethylsulfoxide. N$^6$-Cyclopentyladenosine was dissolved at 10 mM in 0.02N HCl and diluted in Tris. Stock solutions and dilutions of N$^6$-cyclopentyladenosine could be stored at −20° C. for several months. Test compounds were dissolved at 10 mM in dimethylsulfoxide on the same day as the experiment, and diluted in dimethylsulfoxide to 100× the final incubation concentration. Control incubations received an equal volume (10 μl) of dimethylsulfoxide; the resulting concentration of dimethylsulfoxide had no effect on binding. [$^3$H]NECA was diluted to 40 nM in Tris. The membrane suspension (5 mg/0.79 ml) contained sufficient MgCl$_2$ and adenosine deaminase to give 10 mM and 0.1 units/ml, respectively, final concentration in the incubation. For test compounds with IC$_{50}$ values less than 1 μM, the order of additions was test compound (10 μl), N$^6$-cyclopentyladenosine (100 μl), [$^3$H]NECA (100 μl), and membranes (0.79 ml). For test compounds with IC$_{50}$ values greater than 1 μM and limited water solubility, the order of additions (same volumes) was test compound, membranes, N$^6$-cyclopentyladenosine, and [$^3$H]NECA. After all additions, the rack of tubes was vortexed, and the tubes were then incubated for 60 min at 25° C. in a shaking water bath. The rack of tubes was vortexed an additional time halfway through the incubation.

Incubations were terminated by filtration through 2.4 cm GF/B filters under reduced pressure. Each tube was filtered as follows: the contents of the tube were poured onto the filter, 4 ml of ice-cold Tris were added to the tube and the contents poured onto the filter, and the filter was washed twice with 4 ml of ice-cold Tris. The filtration was complete in about twelve seconds. Filters were put in scintillation vials, 8 ml of Formula 947 scintillation fluid added, and the vials left overnight, shaken, and counted in a liquid scintillation counter at 40% efficiency.

Data Analysis

Nonspecific binding was defined as binding in the presence of 100 μM N$^6$-cyclopentyladenosine, and specific binding was was defined as total binding minus nonspecific binding. The IC$_{50}$ was calculated by weighted nonlinear least squares curve-fitting to the mass-action equation.

$$Y = T - S \cdot \frac{D}{D + K}$$

where
Y is cpm bound
T is cpm total binding without drug
S is cpm specific binding without drug
D is the concentration of drug and
K is the IC$_{50}$ of the drug
Weighting factors were calculated under the assumption that the standard deviation was proportional to the predicted value of Y. Nonspecific binding was treated as a very large (infinite) concentration of drug in the computer analysis.

The IC$_{50}$ values (nM) for adenosine A$_1$ and A$_2$ receptor affinity are reported in the table.

| Example Number | Receptor Binding RBA-1 (nm) | RBA-2 (nm) |
| --- | --- | --- |
| 1 | 9 | 19,000 |
| 2 | 7.8 | 11,000 |
| 3 | 46 | 20,000 |
| 4 | 430 | 24,000 |
| 5 | 440 | 15,000 |
| 6 | 940 | 20,000 |
| 7 | 8800 | 23% Inhib at 1 × 10$^{-4}$M |
| 8 | 34 | 75,000 |
| 9 | N* | N* |
| 10 | N* | N* |
| 11 | N* | N* |

*Indicates no activity in this in vitro assay, however, as prodrug forms activity is expected in vivo.

ANTIPSYCHOTIC EVALUATION

The compounds of the invention are new chemical substances which are useful as pharmaceutical agents for the treatment of psychoses. The antipsychotic activity of representative compounds of the invention was established by the Mouse Activity and Screen Test Procedure (MAST) described below.

Animals

Nine unfasted Swiss-Webster male mice weighing 20–30 g are equally divided into three groups for each drug dose to be tested. That is, data for each dose level was generated by three separate groups of three mice each.

Drugs

A minimum of three dose levels (10, 30, and 100 mg/kg) are tested for each drug. Treatments are administered intraperitoneally one hour prior to testing. All dosages are calculated as parent compound and given in volumes of 10 ml/kg. Compounds are dissolved or suspended in 0.2% Methocel. Control animals are injected with Methocel.

Testing: A two part testing procedure is started one hour postinjection. First, the screen test (ST) is performed (see Pharmac. Biochem. Behav. 6, 351–353, 1977). Briefly this test consists of placing mice on individual wire screens which are then rotated 180 degrees at the start of a 60 second observation period. The number of mice falling off the inverted screen is recorded.

Immediately following the screen test, the final phase of testing is initiated by placing each group of three mice in one actophotometer (Life Sciences, 22, 1067–1076, 1978). The actophotometer consists of a cylindrical chamber whose center is occupied by another cylinder which contains the illumination for six photocells located on the perimeter of the chamber. Six light-beam interruptions equal one count. Locomotor activity is recorded by computer at ten minute intervals for 60 minutes.

Data: The data obtained from the screen test are expressed as percent of mice falling off the screen. Data derived from locomotor activity of drug treated mice are compared to the activity of vehicle treated animals and are expressed as percent inhibition of spontaneous locomotion. All percentages reported for inhibition of locomotion (LI) are based upon data accumulated for one hour. Both phases of testing are graded: A=6-0-100%; C=31-59%; and N=0-30%. An overall dose rating is obtained by the following criteria:

| Inhibition of Locomotion Rating | with | Screen Test Failure Rating | = | Dose Rating |
|---|---|---|---|---|
| A | — | N or C | = | A |
| A | — | A | = | C |
| C | — | N or C | = | C |
| All other combinations | | | = | N |

LAD refers to the lowest dose at which an A rating is achieved. Compounds which exhibit an overall dose rating of A at a dose of 100 milligrams/kilogram or less are considered active. Utilizing this procedure, an overall dose rating of A was obtained for the noted compound at the indicated dose. The compounds are identified in the Examples.

| Example | Dose (mg/kg) | Inhibition of Mouse Locomotor Activity | Screen Test Failure |
|---|---|---|---|
| 1 | 0.1 | 46% | 8% |
|   | 0.3 | 96% | 100% |
|   | 1.0 | 97% | 100% |
|   | 3.0 | 99% | 100% |
|   | 10 | 100% | 100% |
|   | 30 | 100% | 100% |
|   | 100 | 99% | 100% |
| 2 | 10 | 100% | 100% |
|   | 30 | 100% | 100% |
|   | 100 | 100% | 100% |
| 3 | 0.03 | −19% | 0% |
|   | 0.1 | −18% | 0% |
|   | 0.3 | 0% | 0% |
|   | 1.0 | 92% | 88% |
|   | 3.0 | 97% | 100% |
|   | 10 | 97% | 100% |
|   | 30 | 100% | 100% |
| 4 | 0.3 | 6% | 0% |
|   | 1.0 | 27% | 0% |
|   | 3.0 | 23% | 0% |
|   | 10 | 96% | 66% |
|   | 30 | 93% | 99% |
|   | 100 | 99% | 99% |
| 5 | 0.3 | 40% | 0% |
|   | 1.0 | 39% | 11% |
|   | 3.0 | 69% | 11% |
|   | 10 | 48% | 77% |
|   | 30 | 98% | 100% |
| 6 | 3 | 26% | 0% |
|   | 10 | 47% | 0% |
|   | 30 | 71% | 0% |
| 7 | 3 | 13% | 11% |
|   | 10 | 18% | 0% |
|   | 30 | 69% | 0% |
| 8 | 0.3 | 56% | 0% |
|   | 1.0 | 98% | 88% |
|   | 3.0 | 98% | 99% |
|   | 10 | 99% | 99% |
|   | 30 | 100% | 99% |
|   | 100 | 99% | 99% |
| 9 |   | Not Tested |   |
| 10 |   | Not Tested |   |
| 11 | 3 | 59% | 22% |
|   | 10 | 91% | 55% |
|   | 30 | 79% | 100% |

ANALGESIC EVALUATION

The antiwrithing (AW) test provides preliminary assessment of compounds with potential analgesic activity. The test is performed in male Swiss-Webster mice. Compounds are administered subcutaneously in aqueous 0.2% methylcellulose or other appropriate vehicles in volumes of 10 ml/kg. Dosages represent active moiety.

Acetic acid (0.6%, 10 ml/kg) is injected intraperitoneally 20 minutes after administration of the adenosine agonist. Writhing movements are counted for five minutes starting seven minutes after the acetic acid injection. Writhing is defined as abdominal constriction and stretching of the body and hind legs with concave arching of the back. Data are expressed as $ED_{50}$ values, where the $ED_{50}$ is the dose necessary to suppress writhing by 50% relative to vehicle controls. $ED_{50}$ values are calculated by nonlinear regression analysis. Thus, for example, the compound of Example 1 had an $ED_{50}$ in mg/kg of 0.07.

Accordingly, the present invention also includes a pharmaceutical composition for treating sleep disorders or pain comprising a corresponding sedative or analgesic effective amount of a compound of the Formula I as defined above together with a pharmaceutically acceptable carrier.

The present invention further includes a method for treating sleep disorders or pain in mammals suffering therefrom comprising administering to such mammals either orally or parenterally a corresponding pharmaceutical composition containing a compound of the Formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 5 to 100 mg according to the particular application and the potency of the active ingredient. The compositions can, if desired, also contain other compatible therapeutic agents.

In therapeutic use as described above, the mammalian dosage range for a 70 kg subject is from 0.1 to 150 mg/kg of body weight per day or preferably 1 to 50 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples further illustrate the invention.

EXAMPLE 1

(R,S)-$N^6$[2,3-Dihydroxypropyl]adenosine 6-chloropurineriboside (5.8 g, 20 mmol, 2,3-propylaminediol (1.82 g, 20 mmol) and triethylamine (2.02 g, 20 mmol) were combined in 250 ml ethanol and refluxed for 18 hours. Removal of the ethanol gave a viscous syrup. Refluxing ethanol was added to the syrup sufficient to dissolve it, then allowed to cool and stand at 0° for 24 hours. The resulting crystals were filtered and dried, yielding 3.6 g (53%) m.p. 164°-165° analysis for ($C_{13}H_{19}N_5O_6$) Calcd: C=45.74, H=5.61, N=20.52; Found: C=45.93, H=5.49, N=20.63, $H_2O$ 0.70.

EXAMPLE 2

(R)-$N^6$-[2,3-Dihydroxypropyl]adenosine

The title compound was prepared using (R)-$N^6$-[2,3-dihydroxypropylisopropylidine]adenosine from Example 5 (3.4 g, 8.9 mmol) in 100 ml 1:1 water:methanol containing 10% trifluoroacetic acid. The solution was stirred at ambient temperature overnight. After removal of solvents, the residue was co-distilled with ethanol (5×100 ml) to give a white foam. This foam was recrystallized from ethanol to yield 1.5 g product m.p. 120°-125° analysis for ($C_{13}H_{19}N_5O_6$). Calcd: C=45.74, H=5.61, N=20.52; Found: C=45.12, H=5.73, N=19.09.

H' NMR (DMSO-$d_6$, 60 MHz): δ 3.25-3.8 (m, 7H), δ 3.92 (m, 1H), δ 4.1 (m, 1H), δ 4.55 (br.t, 1H), δ 5.15 (br.m, 6H) [$H_3O^+$], δ 5.85 (d, 1H), δ 7.7 (br.s, 1H), δ 8.2 (s, 1H), δ 8.35 (s, 1H).

EXAMPLE 3

(S)-$N^6$-[Dihydroxypropyl]adenosine

The title compound was prepared with material from Example 6, (S)-$N^6$-[Dihydroxypropylisopropylidene]adenosine (2.3 g, 6 mmol). This was placed in 20% acetic acid in 1:1 methanol:water (100 ml), and stirred at ambient temperature for 22 hours. After removal of solvents, the residue was treated with acetone and the resulting percipitate filtered and dried in vacuo. This was then redissolved in 15% acetic acid, 1:1 water:methanol and stirred another 48 hours. Removal of solvents and vacuum drying at 85° yielded 0.77 g final product. m.p. 231°-5°

Analysis for ($C_{13}H_{19}N_5O_6$) Calcd: C=45.74, H=5.61, N=20.52; Found: C=44.78, H=5.23, N=19.34.

H'NMR (DMSO-$d_6$, 60 MHz): δ 3.3-3.9 (m, 7H), δ 3.95 (q, 1H), δ 4.15 (s, 1H), δ 4.6 (br.s, 2H), δ 4.85 (br.s, 1H), δ 5.15 (br.s, 1H), δ 5.35 (br.m, 2H), δ 5.9 (d, 1H), δ 7.5 (br.t, 1H), δ 8.2 (s, 1H), δ 8.35 (s, 1H).

EXAMPLE 4

(R,S)-$N^6$-[2,3Dihydroxypropylisopropylidene]adenosine

The title compound was prepared as in Example 1 using 2.6 g (20 mmol) dihydroxypropylisopropylidene amine, 5.7 g (20 mmol) 6-chloropurineriboside and 2.02 g (20 mmol) triethylamine. m.p. 155°-159°.

Analysis for ($C_{16}H_{23}N_5O_6$) Calcd: C=50.39, H=6.08, N=18.36; Found: C=50.11, H=6.11, N=18.31, $H_2O$=1.48.

EXAMPLE 5

(R)-N⁶-[2,3-Dihydroxypropylisopropylidene]-adenosine

The title compound was prepared as in Example 1 using 5.7 g (20 mmol) 6-chloropyrineriboside, (R)-2,3-dihydroxypropylisopropylidineamine 2.6 g (20 mmol), and 2.0 g (20 mmol) triethylamine. m.p. 154°–160°.

Analysis for ($C_{16}H_{23}N_5O_6$) Calcd: C=50.39, H=6.08, N=18.36; Found: C=50.22, H=6.21, N=18.51, $H_2O$=0.65.

The starting amine was prepared as follows: 21.7 g (0.164 m) of the commercially available (R)2,3-isopropylidene glycerol was dissolved in 100 ml pyridine and cooled to 0°. To this tosylchloride (31.3 g, 0.164 m) was added and the solution stirred for 15 min. It was then kept at 8° for 72 hours. The cold solution was poured into a mixture of 400 ml ether and 200 ml water and the ethereal portion separated. Additional ether was added to the aqueous solution, shaken, and separated. The combined ethereal solutions were washed with 1N HCl (4×150 ml), followed by water, then saturated brine. Finally, after drying over $MgSO_4$ the ether was removed to give a clear oil. ($C_{12}H_{16}O_5S$). Calcd: C=54.53, H=6.29, S=11.22; Found: C=54.00, H=6.34, S=11.50.

This clear oil was reduced in a sealed tube using ammonia at room temperature for 94 hours. To this mixture was added THF, the reaction mixture filtered and the filtrate concentrated. After distillation (38° C., 1.2 mm), 7.9 g clear oil was obtained. Analysis as ($C_{16}H_{13}O_2N$). Calcd: C=54.94, H=9.99, N=10.68; Found: C=55.26, H=9.72, N=10.74.

EXAMPLE 6

(S)-N⁶-[2,3-Dihydroxypropylisopropylidene]adenosine

The title compound was prepared as in Example 1 using 5.7 g (20 mmol) 6-chloropyrineriboside, 2.6 g (20 mmol) (S)-2,3dihydroxypropylisopropylideamine* and 2.02 g (20 mmol) triethylamine. m.p. 102°–104°.
*Preparation from J. Am. Chem. Soc., 64, 1291 (1942).

Analysis for ($C_{16}H_{23}N_5O_6$). Calcd: C=50.39, H=6.08, N=18.36; Found: C=49.23, H=6.12, N=18.35, $H_2O$=0.88.

H' NMR (DMSO-d₆, 200 MHz): δ 1.25 (s, 3H), δ 1.35 (s, 3H), δ 3.34–3.81 (m, 5H), δ 3.93 (sh.m, 2H), δ 4.14 (br.s, 1H), δ 4.31 (pent, 2H), δ 4.61 (q, 1H), δ 5.20 (d, 1H), δ 5.40 (s, 1H), δ 5.45 (d, 1H), δ 5.89 (d, 1H), δ 7.9 (br.s, 1H), δ 8.23 (s, 1H), δ 8.38 (s, 1H).

EXAMPLE 7

(R,S)-N⁶-[2,3-Dihydroxypropyl-isopropylidine]-5'-deoxyadenosine 2.8 g (10.8 mmol) 1,2,3-tri-O-acetyl-5'-deoxyribose[1] and 2.7 g (10.8 mmol) N⁶-[2,3-dihydroxypropylisopropylidine]purine were combined, then heated to 165° under a nitrogen atmosphere. To this was added 0.1 ml conc. sulfuric acid, then stirred for three hours. Upon cooling, the solution became a solid, which was treated with ethylacetate to produce a slurry. This slurry was applied to a silica gel column and eluted with ethyl acetate. Fractions with Rf=0.38 were collected, combined, and concentrated. This residue (1.3 g, 2.9 mmol) was taken up in methanol and treated with one equivalent sodium methoxide. After stirring three hours at ambient temperature the methoxide was quenched using Dowex 50×8 resin. The resin was filtered and washed with methanol, and the combined methanolic portions coevaporated with ether to give the product as a tan foam.
[1]Helv. Chim. Acta. 65 (5), 1522 (1982).

Analysis for ($C_{16}H_{23}N_5O_5$) Calcd: C=52.59, H=6.34, N=19.17; Found: C=51.58, H=6.12, N=17.07.

H' NMR (DMSO-d₆, 60 MHz); δ 1.3 (br.d, 9H), δ 3.5–4.1 (m, 6H), δ 4.3 (br.t, 2H), δ 4.6 (br.t, 2H), δ 5.8 (d, 1H), δ 7.75 (br.t, 1H), δ 8.2 (s, 1H), δ 8.3 (s, 1H).

The starting purine was prepared as follows: 2.1 g (10 mmol) N⁶-[2,3-dihydroxypropyl]purine was put into 150 ml acetone with 12 ml dimethoxypropane and 3.75 g (11 mmol) Hampton's catalyst[2] and stirred for 19 hours at ambient temperature. The reaction was quenched by stirring 100 ml 15% aqueous sodium bicarbonate, the acetone removed under reduced pressure, and the aequeous solution extracted with methylene chloride (3×100 ml). After drying, the combined organic layers were concentrated to a yellow-solid, which was then dissolved in methanol and passed through a Dowex (1×8, 400 mesh, $NH_4^+HCO_3^-$ form')-column. Evaporation of the solvent gave the final product, which was used in the synthesis of the title compound.
[2]J. Am. Chem. Soc. 83, 3640 (1961).

EXAMPLE 8

(R,S)-N⁶-[Dihydroxypropyl]-2-amino-adenosine

The title compound was prepared as in Example 1 using 3.0 g (10 mmol) 2-amino-6-chloropurineriboside, 0.9 g (10 mmol) 2,3-dihydroxypropylamine and 1.0 g (10 mmol) triethylamine. the product was collected as a glass.

Analysis for ($C_{13}H_{20}N_6O_6$) Calcd: C=43.82, H=5.66, N=23.58; Found: C=43.21, H=5.85, N=22.73.

H' NMR (DMSO-d₆, 60 MHz): δ 3.20–3.7 (m, 7H), δ 3.85 (br.q, 1H), δ 4.1 (br.s, 1H), δ 4.45 (br.s, 1H), δ 5.2 (br.m, 5H), δ 5.7 (d, 1H), δ 5.9 (br.s, 2H), δ 7.05 (br.t, 1H), δ 7.9 (s, 1H).

EXAMPLE 9

N-6[2,3-Dihydroxypropyl-2,3-di-O-propionyl]adenosine-2',3',5'-tri-O-propionyl

The adenosine compound from Example 1 (2.0 g, 6 mmol) was dissolved in pyridine (50 ml) and treated with propionic anhydride (5.2 g, 40 mmol) and the solution stirred at room temperature, overnight. The pyridine was evaporated in vacuo and the residue dissolved in methylene chloride (100 ml). The solution was washed successively with 2% sodium bicarbonate (100 ml), 1N HCl (100 ml), water (100 ml) and saturated salt solution (100 ml). The organic solution was dried over magnesium sulfate and the solvents evaporated in vacuo. The residue was dissolved in ethylacetate (25 ml) and purified by chromatography. The major fraction was evaporated in vacuo to give 2.2 g (59%) of the product as a light yellow oil.

Analysis for ($C_{28}H_{39}N_5O_{11}$); Calcd: C=54.10, H=6.32, N=11.27; Found: C=54.33, H=6.48, N=11.16.

EXAMPLE 10

N-6[2,3-Dihydroxypropyl-2,3-isopropylidene]2',3',5'-tri-O-isovaleroyl adenosine

The adenosine analog from Example 4 (3.0 g, 7.9 mmol) was dissolved in pyridine (50 ml) and treated with iso-valeric anhydride (5.8 g, 31.4 mmol) and the solution stirred at room temperature, overnight. The solution was evaporated free of pyridine, in vacuo, and the residue dissolved in methylene chloride (100 ml). The solution was washed successively with 2% sodium bicarbonate (100 ml), 1N HCl (100 ml), water (100 ml), and finally saturated salt solution (100 ml). The organic solution was dried over magnesium sulfate and the the solvents evaporated in vacuo to give an oil. The oil was dissolved in 25 ml of ethylacetate and purified by chromatography to give, after evaporation of solvent from the major fraction, 2.85 g (57%) of the product as a light yellow oil.

Analysis for ($C_{31}H_{47}N_5O_9$): Calcd: C=58.75, H=7.48, N=11.05; Found: C=58.63, H=7.68, N=10.78.

EXAMPLE 11

N-6[2,3-Dihydroxypropyl-2,3-di-O-isovaleroyl]-2',3',5'-tri-O-isovaleroyl adenosine The title compound was prepared in a manner analogous to Example 9 using the adenosine analog from Example 1 (2.0 g, 6 mmol) and isovaleric anhydride (7.5 g, 40 mmol) in pyridine (50 ml). The product was isolated as a yellow oil, 2.8 g (61%).

Analysis for ($C_{38}H_{59}N_5O_{11}.0.25C_5H_{10}O_2$) Calcd: C=59.87, H=7.87, N=8.89; Found: C=59.59, H=8.08, N=8.89.

We claim:

1. A compound of the formula

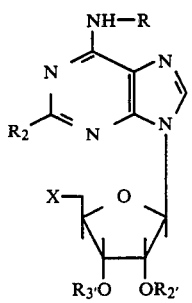

wherein R is

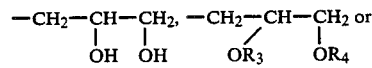

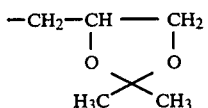
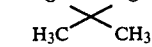

wherein $R_3$ and $R_4$ are the same or different and are lower alkanoyl, benzoyl, or benzoyl substituted by lower alkyl, lower alkoxy, halogen, or trifluoromethyl; $R_2$ is H, $NH_2$, $NHR_6$ where $R_6$ is alkanoyl, benzoyl, or benzoyl substituted by lower alkyl, lower alkoxy, halogen, or trifluoromethyl; or halogen; $R_2'$ and $R_3'$=H, lower alkanoyl, benzoyl or benzoyl substituted by lower alkyl, lower alkoxy, halogen or trifluoromethyl, or when taken together lower alkylidene; X is OH, acetyloxy, H, Cl, $SCH_3$, or $OR_5'$ wherein $R_5'$ is H, lower alkanoyl, benzoyl, benzoyl substituted by lower alkyl, lower alkoxy, halogen, or trifluoromethyl; its diastereomers or mixtures thereof, or a pharmaceutically acceptable acid addition salt thereof.

2. A compound according to claim 1, wherein R is 2,3-dihydroxypropyl.

3. A compound according to claim 2, wherein $R_2$ is hydrogen.

4. A compound according to claim 3, wherein $R_2'$ and $R_3'$ are hydrogen.

5. A compound according to claim 4 and being $N^6$-(2,3-dihydroxypropyl)adenosine.

6. A compound according to claim 1 wherein R is

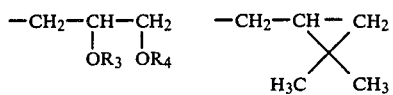

7. A compound according to claim 6 and being N-6[2,3-Dihydroxypropyl-2,3-di-O-propionyl]-2',3',5'-tri-O-propionyl adenosine.

8. A compound according to claim 6 and being N-6[2,3-Dihydropropyl-2,3-isopropylidene]2',3',5'-tri-O-isovaleryl adenosine.

9. A compound according to claim 6 and being N-6[2,3-dihydroxypropyl-2,3-di-O-isovaleroyl]-2',3',5'-tri-O-isovaleroyl adenosine.

10. A pharmaceutical composition for treating sleep disorders comprising an effective amount for treating sleep disorders of a compound as claimed in claim 1 together with a pharmaceutically acceptable carrier.

11. A method of treating sleep disorders in a mammal suffering therefrom comprising administering to such mammal a sedative effective amount of a compound as claimed in claim 1 in unit dosage form.

12. A compound according to claim 6 and being (R)-$N^6$-[2,3-dihydroxypropyl]adenosine.

13. A compound according to claim 6 and being (S)-$N^6$-[dihydroxypropyl]adenosine.

14. A compound according to claim 6 and being (R)-$N^6$-[2,3-dihydroxypropylisopropylidene]adenosine.

15. A compound according to claim 6 and being (S)-$N^6$-[2,3-dihydroxypropylisopropylidene]adenosine.

* * * * *

UNITED STATES PATENT AND TRADEMARK OFFICE
CERTIFICATE OF CORRECTION

PATENT NO. : 4,616,003
DATED : 7 OCTOBER, 1986
INVENTOR(S) : HARRIET W. HAMILTON, ET AL.

It is certified that error appears in the above—identified patent and that said Letters Patent is hereby corrected as shown below:

Column 2, line 10;  Change "$\overset{O}{\underset{}{C}}$-alkyl" to  --$\overset{O}{\underset{}{\overset{\|}{C}}}$-alkyl--

Column 2, line 38;  Change "atoms." to --atom.--

Signed and Sealed this

Fourteenth Day of April, 1987

Attest:

DONALD J. QUIGG

Attesting Officer

Commissioner of Patents and Trademarks